United States Patent [19]
Addington et al.

[11] Patent Number: 5,904,656
[45] Date of Patent: *May 18, 1999

[54] ASPIRATION SCREENING PROCESS FOR ASSESSING NEED FOR MODIFIED BARIUM SWALLOW STUDY

[75] Inventors: W. Robert Addington, Indialantic, Fla.; Robin R. Ockey, San Antonio, Tex.; Robert E. Stephens, Parkville, Mo.

[73] Assignee: Dysphagia Systems, Inc., Melbourne, Fla.

[*] Notice: This patent is subject to a terminal disclaimer.

[21] Appl. No.: 08/885,360

[22] Filed: Jun. 30, 1997

Related U.S. Application Data

[63] Continuation of application No. 08/559,562, Nov. 16, 1995, Pat. No. 5,678,563.

[51] Int. Cl.$^6$ ........................................... A61B 5/08
[52] U.S. Cl. ........................................ 600/529; 128/898
[58] Field of Search .................................. 600/300, 529, 600/533, 586, 593; 128/204.21, 204.22, 204.23, 204.12, 898

[56] References Cited

U.S. PATENT DOCUMENTS

| | | | |
|---|---|---|---|
| 4,558,710 | 12/1985 | Eichler | 600/533 |
| 5,024,240 | 6/1991 | McConnel | 600/593 |
| 5,143,087 | 9/1992 | Yarkony | 600/593 |
| 5,678,563 | 10/1997 | Addington et al. | 600/529 |

OTHER PUBLICATIONS

Horner et al., "Silent aspiration following stroke," Neurology, vol. 38, pp. 317–319, Feb. 1998.

DePippo et al., "Validation of the 3–oz Water Swallow Test for Aspiration Following Stroke," Archives of Neurology, vol. 49, pp. 1259–1261, Dec. 1992.

Florida Hospital Association 1996 "Cost of Dysphagia Testing and treatment of Aspirating Pneumonia." (single sheet) dated Sep. 24, 1997.

Merck Index. 12th ed. 1996 "Tartaric Acid", p. 1552.

(List continued on next page.)

Primary Examiner—Cary O'Connor
Assistant Examiner—Eric F. Winakur
Attorney, Agent, or Firm—Charles E. Wands

[57] ABSTRACT

Whether a (stroke) patient is at risk for oral or pharyngeal dysphagia is determined by conducting a cough-based screening process for clinically evaluating the patient's swallow. The cough-based screening methodology is able to identify those patients who require a modified barium swallow test in order to rule out aspiration, and which patients do not need a modified barium swallow test. In accordance with the process the patient attempts to cough voluntarily. If the patient is unable to cough voluntarily, the patient is required to inhale an aerosol that stimulates a sensory innervation of the patient's larynx, thereby causing the patient to cough. The resulting cough is graded to determine whether the patient is at risk to a prescribed physiological condition, in particular pneumonia. The cough tests are supplemented by monitoring the ability of the patient to hold water in the patient's mouth for a prescribed period of time. If the patient is able to hold a prescribed volume of water in the patient's mouth for the prescribed period of time, the patient is permitted to be given a modified barium swallow test. If the patient is unable to hold a prescribed volume of water in the patient's mouth for the prescribed period of time, the patient is not permitted to be given a modified barium swallow test.

8 Claims, 7 Drawing Sheets

United States Department of Labor, Occupational Safety and Health Administration. material Safety Data Sheet (MSDS) on Tartaric Acid (2 sheets).

Addendum to MSDS on Tartaric Acid. "Regulatory Status" (6 sheets).

Partial Listing of OTC Inhalers with Bitartrate. (Single Sheet).

Patty's Industrial Hygiene and Toxicology Volume 2C 1982 "Tartaric Acid" pp. 4937,4743–5, 4981–2.

Chasseaud LF, Down WH, Kirkpatrick D. 1977 Absorption and Biotransformation of L(+)–Tartaric Acid in Rats.

Fassett DW. Organic Acids, Anhydrides, Lactones, Acid Halides and Amides, Thioacids in Industrial Hygiene and Toxicology 2nd ed. vol. II. DW Fassett and DD Irish, eds., Wiley–Interscience, New York. 1963. pp. 1771–1777, 1811, 1814.

Fithugh OG, Nelson AA. 1947 The Comparative Chronic Toxicities of Fumaric, Tartaric, Oxalic and Maleic Acids. J AM Pharm Assocs 36:217–9.

Horn HJ, Holland EG, Hazleton LW. 1957 Safety Adipic Acid as Compared with Citric and Tartaric Acid. J Agric Food Chem 5:759–61.

Lewis JD. 1977 Comparison of the Distribution of L(+) and DL–Forms of Tartaric Acid in the Rat. Acta Pharmacol Toxicol 41:144–5.

Locke A, Locke RB, Schlesinger H, Carr H. 1942 The Comparative Toxicity and Cathartic Efficiency of Disodium Tartrate and Fumarate, and Magnesium Fumarate for the Mouse and Rabbit, J AM Pharm Assoc 31;12–14.

Smyth Jr. HF, Carpenter CO, Weill CS, Pozzani UC, Striegel JA. 1962 Range–Finding Toxiicity Data: List VL Am Ind. Hyg. ASsoc J23:95–107.

Sourkes TL, Koppanvi T. Correlation Between the Acute Toxicity and the Rate of Eliminatioin of Tartaric Acid and Certain of its Esters 1950. J AM Pharm Assoc. 39:275–6.

Underhill FP, Leonard CS, Gross EG, Jaleski, TC. 1931. Studies on the Metabolism of Tartrates: II The Behavior of Tartrate in the Organism of the Rabbit, Dog, Rat and Guinea Pig. J Pharmacol 43:359–80.

Weiss JM, Downs CR, Corson HP. 1923 Inactive Malic Acid as a Food Acidulent. Ind Eng Chem 15:628–30. Also cited by Registry of Toxic Effects of Chemical Substances, NIOSH ed., 1978.

WHO Food Additives Series, No. 5, "Toxicological Evaluation of Some Food Additives Including Anticaking Agents, Antimocrobials, Antioxidants, Emulsifiers and Thickening Agents." [17th Report of the Joint FAO/WHO Expert Committee on Food Additives, SHO Technical Report Series, 1974, No. 539; FAO Nutrition Meetings Report Series, 1974, No. 53] Geneva. pp. 14, 222–224, 236–237, 512–514.

Addington WR, Stephens RE, Ockey RR, Kann D, Rodriguez M. A New Aspiration Screening Test to Assess the Need for Modified Barium Swallow Study. Archives of Physical Medicine and Rehabilitation Nov. 1995:76(11):1040.

Addington WR, Stephens RE, Gilliland K, Miller SP. The Laryngeal Evoked Potential (LEP) and Laryngeal Cough Reflex, Muscle and Nerve, Aug. 1997; 20(3); 1071–1072.447.

Alberts MJ, Horner J, Gray L. Brazer SR. Aspiration After Stroke: Lesion analysis by Brain MRI Disphagia. 7(3):170–3, 1992.

Alessi DM, Berci G. Aspiration and Nasogastric Intubation. Otolaryngology—Head and Neck Surgery. 94(4):486–9, Apr. 1986.

Aubert M, Guilhen C. Topographie des Projections de la Sensibilite Viscerale Sur L'ecorce Cerebrale du Chat. 3. Etude des Projections Corticales du Nerf Larynge Superieur. Archives Italiennes de Biologie Nov. 1971:109(3):236–52.'

Bandler R, Tork I. Midbrain Periaqueductal Grey Region in the Cat has Afferent and Efferrent Connections with Solitary Tract Nuclei. Neuroscience Letters Feb. 10, 1987; 74(1):106.

Barillot JC, Mei N. Modification, Au Niveau du Noyau de Faisceau Solitaire, de l'Excitabilite des Terminaisons de Fibres Vagales ou Laryngees d'origine connue. 1964 Etude Unitaire, pp. 395–396.

Berger AJ. Dorsal Respiratory Group Neurons in the Medulla of Cat: Spinal Projections, Responses to Lung Inflation and Superior Laryngeal Nerve Stimulation. Brain Research Oct. 28, 1977; 35(2):231–54.

Berkley KJ, Schofield SL. Relays from the Spinal Cord and Soitary Nucleus Through the Parabrachial Nucleus to the Forebrain in the Cat. Brain Research Oct. 8, 1990; 529 (1–2):333–8.

Boushey, HA, Richardson PS, Widdicombe JG. Reflex Effects of Laryngeal Irritation on the Pattern of Breathing and Total Lung Resistance. Journal of Physiology Jul. 1972;224(2);501–13.

Boushey HA, Richardson PS, Widdicombe JF, Wise JC. The Response of Laryngeal AFferent Fibers to Mechanical and Chemical Stiimuli. Journal of Physiology Jul. 1974;240(1):153–75.

Callanan D, Dixon M, Widdicombe JG, Wise JC. Responses of Geese to Inhalation of Irritant Gases and Injections of Phenyl Diguanide, Respiration Physiology (1974) pp. 157–166.

Car A, Jean A, Roman C. A Pontine Primary Relay for Ascending Projections of the Superior Laryngeal Nerve. Exp. Brain Res. 1975; 22:197–210.

Choudry NB, Fuller RW. Sensitivity of the Cough Reflex in Pateints with Chronic Cough. European Respiratory Journal 5(3):296–300, Mar. 1992.

Chung, K, Ambrogio F, Sant Ambrogio G. The Fiber composition of the Superior Laryngeal Nerve. FASEB Journal 1993: 7:A402.

Daniels SK, Brailey K, Priestly DH, Herrington LR, Weisberg LA, Foundas AL. Aspiration in Patients with Acute Stroke. Arch Phys Med Rehabil vol 79, Jan. 1998, pp. 14–19.

Das RM, Jeffery PK, Widdicombe JG. The Structure and Function of Intra–Epithelial Nerve Fibers of the REspiratory Tract in the Cat [proceedings]. Journal of Physiology Aug. 1977;270(1):39P–40P.

Buchholz, DW. Dysphagia Associated with Neurological Disorders [Review] Acta Oto–Rhino–Laryngologica Belgica. 48(2):143–55,1994.

DePippo KL, Holas MA, Reding MJ. Validation of the 3 oz. Water Swallow Test for Aspiration Following Stroke. Arch. Neurol. Feb. 1994, vol. 5, pp. 119–120.

Dvachenko YE, Preobrazhensky NN. Funktsional'naia Differentsiatsiia Afferentov Verkhnegortannogo Nerve Koshki. [Russian: Functional Differentiation of Afferents of Superior Laryngeal Nerve in the Cat]. Neirofiziologiia 1984;16(6):777–83.

Droulias C, Tzinas S, Harlaftis N, Akin JT Jr. Gray, SW, Skandalakis, JE. The Superior Laryngeal Nerve. American Surgeon Sep. 1976;42(0:635–8.

Fujimura M, Sakamoto S, Kamio Y, Matsuda T. Cough Receptor Sensivity and Bronchial Responsiveness in Normal and Asthmatic Subjects. European Respiratory Journal Mar. 1992;5(3):291–5.

Fujimura M, Sakamoto S, Kamio Y, Matsuda T. Effects of Methacholine Induced Bronchoconstriction and Procateral Induced Bronchodilation on Cough Receptor Sensivity to Inhaled Capsaicin and Tartaric Acid. Thorax Jun. 1992;47(6):441–5.

Fujimura M, Sakamoto S, Kamio Y, Matsuda T. Sex Difference in the Inhaled Tartaric Acid Cough Threshold in Non–Atopic Healthy Subjects. Thorax Aug. 1990;45(8):633–4.

Fukuyama T, Umezaki T, Shin T. Detection of Laryngeal Sensory–Evoked Potentials (LSEPs) in the Cat. Oct. 1993 Amer. Academy of Otolaryngology., pp. 748–752.

Fuller R, Hansson L., Karlsson JA. Neurophysiology of the Cough Reflex [Letter]. European Respiratory Journal. 9(3):622–4, Mar. 1996.

Gerhardt T, Bancalari E. Maturational Changes of Reflex Influencing In Newborns. Amer. Physiological Society 1981. pp. 1282–1285.

Glogowska M., Stransky A., Widdicombe JF. Reflex Control of Discharge in Motor Fibers to the Larynx. Journal of Physiology. 239(2):368–79, Jun. 1974.

Guyton AC. Testbook of Medical Physiology (1991, 8th ed.) pp. 402–413.

Guz A, Noble MIM, Widdicombe JF, Trenchard D. Mushin WW. Peripheral Chemoreceptor Block in Man. Respiration Physiology. 1(1):38–40,1966.

Guz A, Noble MIM, Widdicombe JF, Trenchard D., Mushin WW, Markey AR. The Role of Vagal and Glossopharyngeal Afferent Nerves in Respiratory Sensation, Control of Breathing and Arterial Pressure Regulation in Conscious Man. Clinical Science. 39(1):161–70, Feb. 1966.

Hanacek J, Widdicombe JF. Influence of Lung Stretch Receptors on the Cough Reflex in Rabbits, 1983 Lung Stretch and Coughs, pp. 161–168.

Hardy SG. Medullary Projections to the Vagus Nerve and Posterolateral Hypothalamus. Anatomical Record Jun. 1995; 242(2):251–8.

Hedges JE, Bridges CJ. Stimulation of the Cough Reflex. American Journal of Nursing. 68(2):347–8, Feb. 1968.

Holstege G, Meiners L, Tan K. Projections of the Bed Nucleus of the Stria Terminalis to the Mesencephalon, Pons and Medulla Oblongata in the Cat. Experimental Brain Research 1984;58(2):379–91.

Hopkins DA, Holstege G. Amygdaloid Projections to the Mesencephalon, Pons and Medulla Oblongata in the Cat. Experimental Brain Research Aug. 15, 1978; 32(4):529–47.

Horner J, Braser SR, Massey EW. Aspiration in Bilateral Stroke Patients: A Validation Study. Neurology. 43(2):43–3, Feb. 1993.

Horner J, Buoyer FG, Alberts MJ, Helms MJ. Dysphagia Following Brain–Stem Stroke: Clinical Correlates and Outcome. Archives of Neurology Nov. 1991; 48(11):1170–3.

Horner J, Massey EW. Silent Aspiration Following Stroke. Neurology. 38(2):317–9, Feb. 1988.

Horner J, Massey EW, Brazer SR. Aspiration in Bilateral Stroke Patients. Neurology, 40(11):1686–8, Nov. 1990.

Horner J, Massey EW, Riski JE, Lathrop DL, Chase KN. Aspiration Following Stroke: Clinical correlates and Outcome. Neurology. 38(9):1359–62, Sep. 1988.

Iscoe S, Feldman JL, Cohen MI. Properties of Inspratory Termination by Superior Laryngeal and Vagal Stimulation. Respiration Physiology. 35(3):353–66, Apr. 1979.

Javorka K, Tomori Z, Zavarska L. 1985 Upper Airway Reflexes in Newborns with Respiratory Distress Syndrome. pp. 345–349.

Javorka K. Tomori Z, Zavarska L. 1980 Protective and Devensive Airway Reflexes in Premature Infants. Physiologia Bohemoslovaca pp. 29–35.

Jean A. Brainstem Control of Swallowing: Localization and Organization of the Central Pattern Generator for Swalling. 1990 Neurophysiology of the Jaws and Teeth. pp. 294–321.

Jean A, Car A, Roman C. Comparison of Activity in Pontine Versus Medullary Neurones During Swallowing. Experimental Brain Research. 22(2):211–20, 1975.

Jordan D, Donoghue S, Spyer KM. Respiratory Modulation of Afferent Terminal Excitability in the Nucleus Tractus Solitarius. Journal of the Autonomic Nervous System. 3(2–4:2991–7, Apr. 1991.

Jeffrey PK, Korpas J, Widdicombe JF. Intraepithelial Nerve Fibers of the Cat Larynx and the Expiration Reflex [proceedings]. Journal of Physiology. 275:35P, Feb. 1978.

Kamei J, Hosokawa T, Yanaura S, Hukuhara T. Involvement of Central Serotonergic Mechanisms in the Cough Reflex. Japanese Journal of Pharmacology. 42(4):531–8, Dec. 1986.

Kamei J, Hukuhara T, Kasuya Y. Dopaminergic Control of the Cough Reflex as Demonstrated by the Effects of Apomorphine. European Journal of Pharmacology. 141(3):511–3, Sep. 23, 1987.

Karlsson JA. Airway Anaesthesia and the Cough Reflex. [Review] Bulletin European de Physiopathologie Respiratoire. 23 Suppl 10:29s–36s, 1987.

Karlsson JA, Hanson L, Wollmer P, Dahlback M. Regional Sensitivity of the Respiratory Tract to Stimuli Causing Cough and Reflex Bronchoconstriction. Respiratory Medicine Jan. 1991;85 (Supplement A) 47–50.

Karlsson JA, Sant Ambrogio G, Widdicombe J. Afferent Neural Pathways in Cough and Reflex Bronchoconstriction. Journal of Applied Physiology Sep. 1988;65(3):1007–23.

Katsumata U, Sekizawa K, Ebihara T, Sasaki H. Aging Effects on Cough Reflex [letter]. Chest. 107(1):290–1, Jan. 1995.

Kearney HL. Unusual Cases of Cicatricial Stricture of the Esophagus. 1934 OTOL. pp. 527–531.

Kessler JP, Jean A. Inhibition of the Swallowing Reflex by Local Applicaiton of Serotonergic Agents into the Nucleus of the Solitary Tract. European Journal of Pharmacology. 118(1–2:77–84), Nov. 26, 1985.

Kim YH, Hong WO, Kim KM, Kim HY. 1997 Superior Laryngeal Nerve Brain Stem Evoked Response in the Cat. Ann. Otol. Thinol. Laryngol. 106:101–8.

Korpas J. Recent Advances Concerning the Cough Reflex (Chairman's Introduction). [Review] Acta Physiologica Hungarica. 70(2–3:161–5, 1987.

Korpas J, Widdicombe JG. Aspects of the Cough Reflex [Review] Respiratory Medicine. 85 Suppl A:3–5, Jan. 1991.

Lalakea ML, Anonsen CK, Hannley M. Laryngeal Brainstem Evoked Response: A Developmental Study. Laryngoscope 100: Mar. 1990, pp. 294–301.

LeFrock JL, Clark TS, Davies B, Klainer AS. Aspiration Pneumonia. A Ten–Year Review. The American Surgeon May 1979.

Lemere F. Innervation of the Larynx. I. Innervation of Laryngeal Muscles. The American Journal of Anatomy, vol. 51, No. 2, pp. 417–437, 1932.

Lemere F. Innervation of the Larynx. II> Ramus Anastomoticus and Ganglion Cells of the Superior Laryngeal Nerve. American Journal of anatomy 1932; 54:389–107.

Lewis DJ, Prentice DE. The Ultrastructure of a Rat Laryngeal Epithelia. Journal of Anatomy 1980; 130:617–32.

Lowey AD, Burton H. Nuclei of the Solitary Tract: Efferent Projections to the Lower Brain Stem and Spinal Cord of the Cat. Journal of Comparative Neurology Sep. 15, 1978:181(2):421–19.

Lucier GE, Egizil R., Dostrovsky JO. 1986 Projections of the Internal Branch of the Superior Laryngeal Nerve of the Cat. Brain Res. Bull. 15:713–21.

Manchanda AK, Aneia IS. Afferent Projections of Superior Laryngeal Nerve in the Medulla Oblongata—Localization of the 'Swallowing Centre'. Indian Journal of Physiology & Pharmacology. 16(1):67–73, Jan. 1972.

Mantvh PW, Hunt SO. Neuropeptides are Present in Projection Neurones at All Levels in Visceral and Taste Pathways: from Pheriphery to Sensory cortex. Brain Research. 99(2):297–312, May 14, 1984.

Mathew OP, San tAbrogio G, Fisher JT, Sant Ambrogio FB. Respiratory Afferent Activity in the Superior Laryngeal Nerves. Respiration Physiology (1984 58, 41–50.

Matsumoto S. The Activities of Lung Stretch and Irritant Receptors During Cough. Neuroscience Letters, 90(1988) 125–129.

McRitchie DA, Tork I. The Internal Organization of the Human Solitary Nucleus. Brain Research Bulletin 1993;31(1–2):171–93.

Mei NN, Condamin M, Rosseau A. Composition Histologique du Nerf Larynge Superieur de Chat. [Histological Composition of the Superior Laryngeal Nerve of the Cat]. Comptes Rendus des Seances de la Societe de Biologie et de Ses Filiales Jul. 1968; 161(1):145–9.

Mei NN, Nourigat B. Etude Electrophysiologique des Neurones Sensitifs du Nerf Laryne Superieur. [Electrophysiologic Study of the Sensory Neurons of the Superior Laryngeal Nerve]. comptes Rendus des Seances de la Societe de Biologie et de Ses Filliales Jul. 1968; 162(1):149–53.

Miller AD, Bianchi AL, Bishol BO (eds). 1997 Neural Control of the Respiratory Mulcles. Boca Raton CRC Press.

Miller AJ, Loizzi F. Anatomical and Functional Differentiation of Superior Laryngeal Nerve Fibers Affecting Swallowing and Respiration. Experimetal Neurology Feb. 1974;42(2):369–87.

Montalt J, Basterra J, Armengot M, Barona R. Superior Laryngeal Nerve Evoked Potentials: An Experimental Study in the Rabbit. Laryngoscope 104:May 1994, pp. 627–630.

Morice AH, Higgins KS, Yeo WW. Adaptation of Cough Reflex with Different Types of Stimulation. European Respiratory Journal. 5(7):841–7, Jul. 1992.

Neafsey EJ, Hurley–Guis KM, Aranitis D. The Topographical Organization of Neurons in the Rat Medial Frontal, Insular and Olfactory Cortex Projecting to the Solitary Nucleus Olfactory Bulb, Periqueductal Gray and Superior Colliculus. Brain Research. 377(2):561–70, Jul. 9, 1986.

Nishino T, Tagaito Y, Isono S. Cough and Other Reflexes on Irritation of Airway Mucosa in Man. Pulmonary Pharmacology (1996) 9, 285–292.

Nosaka S. Solitary Nucleus Neurons Transmitting Vagal Visceral Input to the Forebrain Via a Direct Pathway in Rats. Expieimental Neurology Sep. 1984;84(3):493–505.

O'Connel F, Thomas VE, Pride NB. Adaptation of Cough Reflex with Different types of Stimulation [letter comment]. Euroean Respiratory Journal. 5(10):1296–7, Nov. 1992.

"FDA Request for Designation", printed Apr. 8, 1998; Sponsor: Disphagia Systems, Inc. pp. 1–9.

"Pneumoflex Neuroscientific Description", FDA Neuroscientific Master; printed Apr. 7, 1998; pp. 1–6.

Pack R.J.., Al—Ugaily L.H., Widdicombe, J.G.—The innervation of the trachea and extrapulmonary bronchi of the mouse. Cell & Tissue Research. 238(1): 61–8, 1984.

Paintal A.S.,—Vagal Sensory Receptors and their Reflex Effects. Physiological Review 1973; 53(1): 159–225 Jan..

Palmer J.B., Duchane A.S.—1991. Rehabilitation of Swallowing Disorders Due to Stroke. Physical Medicine and Rehabilitation Clinics of North America 1991 2(3) 529–546.

Pantaleo T. Corda M.—Expiration–related Neurons in the Region of the Retrofacial Nucleus: Vagal and Laryngeal Inhibitory Influences. Brain Research Dec. 16, 1985; 359(1–2); 343–6.

Pimpaneau A. O'Brien J., Albe–Fessard D.—Afferences du Nerf Larynge Superieur et du Nerf Vague Vers les Aires Corticales de Projections et de Commande de la face, de la Langue et du Larynx Chez le Singe. Journal de Physiologe 1967; 59 (4 Suppl): 474.

Sant' Ambrogio g.—Afferent Pathways for Cough Reflex. [Review] Bulletin European de Physiopathologie Respiratorie 1987; 23 (Suppl 10): 19s–23s.

Sant' Ambrogio g.—1996. Role of the Larynx in Cough.

Sant' Ambrogio G., Mathew O.P., Sant' Ambrogio F.B.—Role of Intrinsic Muscles and Tracheal Motion in Modulating Laryngeal Receptors. Respiration Physiology. 61(3): 289–300, Sep. 1985.

Sant' Ambrogio G., Sant' Ambrogio, F. B., Davies A.—Airway Receptors in Cough. Bulletin Eurpean de Physiopathologie Respiratoire Jan.–Feb. 1984; 20(1): 43–7.

Sant' Ambrogio G., Sant' Ambrogio F. B.,—(1996) Role of Laryngeal Afferents in Cough.

Sant' ambrogio G.G., Tsubone H., Sant' ambrogio F. B,—Sensory Information from the Upper Airway: Role in the Control of Breathing. [Review] Respiration Physiology Oct. 1995; 102(1): 1–16.

Sasaki, C. T., Newman A., Akitava T., Kirchner J.A.—Effect of Microaerosol Inhalation on the Pattern of Breathing. Annals of Otology, Rhinolgy & Laryngology. May–Jun. 1975 84(3 pt 1): 344–9.

Sato I., Shimada K. 1995 Arborization of the Inferior Laryngeal Nerve and Internal Nerve on the Posterior Surface of the Larynx. Clin. Anat. 8:379–387.

Schugt H. P. The Piriform Sinus: Anatomic and Clinical Observations with a Review of the Literature. Arch. Otol. 1940; 31: 626–14. Sekizawa K., Ujiie Y., Nakazawa H., Sasaki H., Katsumata U., Takasugi R. Abnormalities in Cough Reflex. Japanese Journal of Geriatrics, pp. 308–310, v 28, 1991.

Sellick H., Widdicombe, J.G. Vagal Deflation and Inflation Reflexes Mediated by Lung Irritant Receptors, Quarterly Journal of Experimental Physiology, pp. 153–163, v.55, 1970.

Sessle, G. J., Ball, G. J., Lucier, G. E., Suppressive Influences from periaqueductal Gray and Nucleus Raphe Mangus on Respiration and Related Reflex Activities and on Solitary Tract Neurons, and Effect of Naloxone. Brain Research—216 (1981) 145–161.

Shannon, R., Bolser, D. C., Lindsey, G. G. 1997 Neural Control of Coughing and Sneezing. In Neural Control of the Respiratory Muscles. A. D. Miller, A. L. Bianchi, and B. P. Bishop (eds.). Boca Raton: CRC Press, pp. 216–19.

Simonsson, G. B., Jacobs, F. M., Nadel, J.A. Role of Autonomic Nervous System and the Cough Reflex in the Increased Responsiveness of Airways in Patients with Obstructive Airway Disease. Journal of Clinical Investigation. 46(11): 1812–8, Nov. 1967.

Stockwell, M., Lang, S., Yip, R., Zintel, T., White, C., Gallagher, C. G. Lack of Importance of the Superior Laryngeal Nerves in Citric Acid Cough in Humans. Journal of Applied Physiology. 75(2): 613–7, Aug. 1993.

Stockwell, M., Lazanoff, S., Lang, S., Nyssen, J. Superior Laryngeal Nerve Block: An Anatomical Study. 1995 Clinical Anatomy 8:89–95.

Stransky, A., Szereda–Przestaszewska, M., Widdicombe, J.G. The Effects of Lung Reflexes on Laryngeal Resistance and Mutoneurone Discharge. J. Physiol (1973) pp. 417–438.

Suzuki, M., Sasaki, C.T. Effect of Various Sensory Stimuli on Reflex Laryngeal Adduction. Annals of Otology, Rhinology & Laryngology Jan.–Feb. 1997; 86(1 pt 1): 30–6.

Suzuki, M., Sasaki, C. T. Initiation of Reflex Glottic Closure. Annals of Otology, Rhinology & Laryngology May–Jun. 1976; 85(3 pt 1): 382–6.

Szereda–Przestaszewska, M., Widdicombe, J.G. Reflex Changes in the Lumen of the Cat Larynx Due to Chemical Irritation of the Upper Airways. Journal of Physiology—Jul. 1973; 232(2):80p–81p.

Takagi S., Umezaki, T., Shin, T. Convergence of Laryngeal Afferents with Different Natures Upon Cat NTS Neurons. Brain Research Bulletin—vol. 38. No. 3, pp. 261–268, 1995.

Takahama K., Miyata, T. [Cough—Diversity and the Peripheral Mechanisms of Production]. Nippon Yakurigaku Zasshi—Folia Pharmacologica Japonica Feb. 1995; 105(2): 41–52.

Tatar, M., Sant' Ambrogio, G., Sant' Ambrogio, F. B. Laryngeal and Tracheobronichial Cough in Anesthetized Dogs, Journal of Applied Physiology, vol. 76, pp. 2672–2679, 1994.

Tell, F., Fagni, L., Jean, A. Neurons of the Nucleus Tractus Solitarius, in vitro, Generate Bursting Activities by Solitary Tract Stimulation. Exp. Brain Res. (1990) 79: 436–440.

Terreberry, R. R., Neafsey, E/J. Rat Medial Frontal Cortex: A Visceral Motor Region with a Direct Projection to the Solitary Nucleus. Brain Research Nov. 14, 1983; 278 (1–2): 245–9.

Terreberry, R.R., Neafsey, E.J. The Rat Medial Frontal Cortex Projects Directly to Autonomic Regions of the Brainstem. Brain Research Bulletin Dec. 1987; 19 (6): 639–19.

Traxel, R.M., Prudlow, W. F., Kampine, J.P., Coon, R.L., Zuperku, E.J. Annals of Otology, Rhinology & Laryngology. 85(5 pt. 1): 664–9, Sep.–Oct. 1976.

Twitchell, T.E. The Restoration of Motor Function Following Hemiplegia in Man. Brain 1951; 74: 443–80.

van de Kooy, D., Koda, L.Y., McGinty, J.F., Gerfen, C.R., Bloom, F. E. The Organization of Projections from the Cortex, Amygdala, and Hypothalamus to the Nucleus of the solitary Tract in Rat. Journal of Comparative Neurology Mar. 20, 1984: 224(1): 1–24.

van der Kooy, D., McGinty, J.F., Koda, L.Y., Gerfen, C.R., Bloom, F.E. Visceral Cortex: A Direct Connection from Prefrontal Cortex to the Solitary Nucleus in Rat. Neuroscience Letters 1982: 33(2): 123–7.

Vogel, P.H.—The Innervation of the Larynx of Man and the Dog. II. Ramus Anastomoticus and Ganglion Cells of the Superior Laryngeal Nerve. American Journal of Anatomy 1952; 90: 427–47.

Weerasuriva, A., Bieger, D., Hockman, C.H.—Basal Forebrain Facilitation of Reflex Swallowing in the Cat. 1979 Brain Res 174: 119–133.

Widdicombe, J.G.—Sensory Neurophysiology of the Cough Reflex. 1996 J Allergy Clin Immunol 98 (5 part 2): s84–s90.

Widdicombe, J.G.—Neurophysiology of the Cough Reflex 1995 Eur Respir J 8:1193–1202.

Widdicombe, J.G.—Mechanism of Cough and its Regulation [Review] European Journal of Respiratory Diseases—Supplement. 110:11–20, 1980.

Widdicombe, J.G.—Nasal and Pharyngeal Reflexes: Protective and Respiratory Functions. In Respiratory Function of the Upper Airway. G. Sant' Ambrogio and O.P. Mathew, Eds. Marcel Drekker, NY. 1988; pp. 233–58.

Widdicombe, J.G.—Reflexes from the Lungs and the Respiratory Tract. 1971 Acta Physiologica Polonica 22 (3 suppl 2): 397–418.

Widdicombe, J.G.—Sensory Innervation of the Lungs and Airways. Progress in Brain Research 1986; 67:49–64.

Widdicombe, J.G.—Studies on Afferent Airway Innervation. American Review of Respiratory Disease 1977: 115(6 pt 2): 99–105.

Widdicombe, J.G.—Modes of Excitation of Respiratory Tract Receptors. Progress in Brain Research 1976; 43:243–52.

Widdicombe, J.G.—Pulmonary and Respiratory Tract Receptors 1982 J Exp Biol 100:41–57.

Widdicombe, J.G.—Mediators of Reflexes and Bronchoconstriction [Review] European Journal of Rerspiratory Diseases—Supplement. 129:65–94, 1983.

Widdicomber, J.G.—Chemoreceptor Control of Airways 1992—Respiration Physiology 87:373–81.

Widdicomber, J.G.—Lungs and Inspiratory Tract Afferences. Introductory Talk. pp. 233–240. In: Duron B., ed *Respiratory Centers and Afferent Systems.* Paris, INSERM, 1976.

Widdicombe, J.G. [Laryngeal Receptors in the Expiratory Reflex] 1986 Bratislavske Lekarske Listy 85(4): 424–9.

Widdicombe, J.G.—Proceedings: Reflex Control of Larynx. Bulletin de Physio–Pathologie Respiratorie 11(2): 102P–103P, Mar.–Apr. 1975.

Widdicombe, J.G.—Pathophysiology of Lung Reflexes. Bulletin de Physio–Pathologie Respiratorie. 10(1):65–9, Jan.–Feb. 1974.

Widdicombe, J.G.—Lung Reflexes. Bulletin de Physio–Pathologie Respiratorie. 8(3):723–5, May–Jun. 1972.

Widdicombe, J.G.—Reflex Function of the Lung: Round Table Discussion. Bulletin de Physio–Pathologie Respiratorie. 10(1): 85–7, Jan.–Feb. 1974.

Widdicombe, J.G. Glogowska, M.,—Relative Roles of Irritant, Type—J and Pulmonary Stretch Receptors in Lung Reflexes 1973 Acta Neurobiol Exp 33:21–31.

Widdicombe, J.G., Sant' Ambrogio, G., Mathew, O.P.—Nerve Receptors of the Upper Airway, In Respiratory Function of the Upper Airway. G. Sant' Ambrogio and O.P. Mathew, Eds, Marcel Drekker, NY 1988; pp. 193–231.

Widdicombe, J.G., Sterling, G.M.,—The Autonomic Nervous System and Brething [Review] 1970 Archives of Internal Medicine 126:311–29.

Widdicombe, J.G., Tartar, M.—Upper Airway Reflex Control. Annals of the New York Academy of Sciences 1988; 533:252–61.

Yamamoto, Y., Hosono, I., Atoji, Y., Suzuki, Y.—Morphological Study of the Vagal Afferent Nerve Endings in the Laryngeal Mucosa of the Dog 1997 Anatomischer Anzeiger 179:65–73.

Yanaura, S., Hosokawa, T., Kitagawa, H., Yamatake, Y.,—Influence of Tracheal Muscular Tone on the Initiation of Cough Reflex 1978 Japan J. Pharmacol 28(3): 447–455.

Yanaura, S., Kamei, J., Goto, K., Hosokawa, T., Hiramori, T., Misawa, M., Hukuhara, T., –A Quantitative Analysis of the Phrenic Nerve Activities During the Cough Reflex 1982 Folia Pharmacol Japan 79: 543–550.

Yanaura, S., Iwase, H., Sato, S., Nishimura, T.—A New Method for Induction of the Cough Reflex 1974 Japan J. Pharmacol 24(3): 453–460.

Yanaura S., Nishimura, T., Sasao, T., Sone, Y.—Proceedidngs: Pharmacological Studies of the Respiratory Tract. 9. A Study of Cough–Like Reflex. 1974 Japanese Journal of Pharmacology. 24:s29.

Yanaura, S., Nishimura, T. Hosokawa, T., Abe, Y., Iwase, H.—Pharmacological Studies on the Cough–Like Reflex Induced by Chemical Stimulation [Japanese] Nippon Yakurigaku Zasshi—Folia Pharmacologica Japonica. 74(3): 345–52, Apr. 1978.

Yanaura, S. Hosokawa, T., Kitagawa, H., Kamei, J., Misawa, M.—Effects of Peripheral Airway Response on the Cough Reflex. [Japanese] Nippon Yakurigaku Zasshi—Folia Pharmacologica Japonica. 76(8):709–16, Nov. 1980.

Yunaura, S., Hosokawa, T., Kitagawa, H., Misawa, M.—Reflex Effects of Cough Reflex on the Tracheobronichial Vascular Tone. [Japanese] Nippon Yakurigaku Zasshi—Folia Pharmacologica Japonica. 78(1):9–16, Jul. 1981.

Yin, S.S., Qui, W.W., Stucker, F.J., Hoasjoe, D.K., Aarstad, R.F., Batchelor, B.M.—1997 Laryngeal Evoked Brainstem Responses in Humans: A Prelininary Study. Laryngoscope 107:1261–6., Sep. 1997.

Yoshida, Y., Tanaka, Y., lMitsumasu, T., Hirano, M., Kanaseki, T.—1986 Peripheral Course and Intramucosal Distribution of the Laryngeal Sensory Nerve Fibers of Cats. Brain Research Bulletin 17:95–105.

Zelenak, J.P., Alarie, lY., Weyel, D.A.—Assessment of the Cough Reflex Caused by Inhalation of Sodium Lauryl Sulfate and Citric Acid Aerosols. Fundamental & Applied Toxicology. 2(4): 177–80, Jul.–Aug. 1982.

Rogers, R.C., Nelson, D.O.—Neurons of the Vagal Division of the Solitary Nucleus Activated by the Paraventricular Nucleus of the Hypothalamus. Journal of the Autonomic Nervous System Apr. 1984; 10(2): 193–7.

Sekizawa, K., Yjiie, Y., Itabashi, S., Sasaki, H., Takishima, T.—Lack of Cough Reflex in Aspiration Pneumonia. [Letter] Lancet May 19, 1990;335 (8699):1228–9.

| ID# | VOLUNTARY COUGH | ASPIRATION INHALATION TEST COUGH | WATER TEST |
|---|---|---|---|
| 1 | + | − | + |
| 6 | + | + | + |
| 8 | + | − | + |
| 9 | + | + | + |
| 21 | + | − | + |
| 24 | + | + | + |

| MR# | MBS | WATER TEST ||||| ||||| RESPIRATORY TEST |||
| | | H2O 15ML |||| | H2O 30ML |||| | COUGH REFLEX |||
| | | GVN | RTRN | OUT MOUTH | DWN THRT | | GVN | RTRN | OUT MOUTH | DWN THRT | | %CON TART | VOL COUGH | INH COUGH |
|---|---|---|---|---|---|---|---|---|---|---|---|---|---|---|
| 1 | ASP | 15 | 14 | 1 | 0 | | 30 | 30 | 0 | 0 | | 20 | ABSENT | NORM |
| 2 | NO ASP | 7.5 | 7.5 | 0 | 0 | | 25 | 25 | 0 | 0 | | 20 | WEAK | NORM |
| 3 | NO ASP | 15 | 15 | 0 | 0 | | 30 | 29 | 0 | 1 | | 20 | NORM | NORM |
| 4 | NO ASP | 15 | 15 | 0 | 0 | | 30 | 30 | 0 | 0 | | 20 | WEAK | WEAK |
| 5 | PEN | 15 | 0 | 0 | 15 | | 30 | 20 | 0 | 10 | | 20 | NORM | NORM |
| 6 | ASP | 15 | 15 | 0 | 0 | | 30 | 25 | 0 | 5 | | 20 | WEAK | WEAK |
| 7 | NO ASP | 15 | 10 | 0 | 5 | | 30 | 0 | 0 | 30 | | 20 | WEAK | NORM |
| 8 | ASP | 15 | 14 | 0 | 1 | | 30 | 30 | 0 | 0 | | 20 | WEAK | NORM |
| 9 | ASP | 15 | 15 | 0 | 0 | | 30 | 29 | 0 | 1 | | 20 | ABSENT | WEAK |
| 10 | NO ASP | 15 | 15 | 0 | 0 | | 30 | 10 | 0 | 20 | | 20 | NORM | NORM |
| 11 | PEN | 15 | 14 | 1 | 0 | | 30 | 20 | 0 | 10 | | 20 | NORM | NORM |
| 12 | NO ASP | 15 | 15 | 0 | 0 | | 30 | 30 | 0 | 0 | | 20 | NORM | NORM |
| 13 | NO ASP | 15 | 10 | 5 | 0 | | 30 | 25 | 5 | 0 | | 20 | NORM | NORM |
| 14 | PEN | 15 | 15 | 0 | 0 | | 30 | 30 | 0 | 0 | | 20 | NORM | NORM |
| 15 | NO ASP | 15 | 14 | 1 | 0 | | 30 | 15 | 0 | 15 | | 20 | WEAK | WEAK |
| 16 | PEN | 15 | 9 | 0 | 6 | | 30 | 4 | 0 | 26 | | 20/50 | WEAK | WEAK |
| 17 | PEN | 15 | 0 | 0 | 15 | | 30 | 0 | 0 | 30 | | 20 | WEAK | NORM |
| 18 | NO ASP | 15 | 10 | 0 | 5 | | 30 | 10 | 0 | 20 | | 20 | WEAK | NORM |
| 19 | PEN | 15 | 1 | 5 | 9 | | 30 | 15 | 5 | 10 | | 20 | WEAK | NORM |
| 20 | NO ASP | 15 | 0 | 1 | 14 | | PT UNABLE TO TOLERATE TEST |||| | 20 | NORM | NORM |
| 21 | ASP | 15 | 14 | 1 | 0 | | 30 | 25 | 5 | 0 | | 20 | WEAK | NORM |
| 22 | NO ASP | 15 | 14 | 1 | 0 | | 30 | 25 | 5 | 0 | | 20 | WEAK | WEAK |
| 23 | PEN | 15 | 15 | 0 | 0 | | 30 | 30 | 0 | 0 | | 20 | WEAK | NORM |
| 24 | ASP | 15 | 10 | 5 | 0 | | 30 | 0 | 30 | 0 | | 20 | WEAK | WEAK |
| 25 | NO ASP | 15 | 15 | 0 | 0 | | 30 | 29 | 1 | 0 | | 20 | NORM | NORM |
| 26 | NO ASP | 15 | 15 | 0 | 0 | | 30 | 30 | 0 | 0 | | 20 | NORM | NORM |
| 27 | NO ASP | 15 | 15 | 0 | 0 | | 30 | 30 | 0 | 0 | | 20 | NORM | NORM |
| 28 | PEN | 15 | 10 | 0 | 5 | | 30 | 0 | 0 | 30 | | 20 | WEAK | NORM |
| 29 | NO ASP | 15 | 15 | 0 | 0 | | 25 | 25 | 0 | 0 | | 20 | NORM | NORM |
| 30 | NO ASP | 15 | 15 | 0 | 0 | | 30 | 29 | 1 | 0 | | 20/50 | WEAK | WEAK |
| 31 | NO ASP | 15 | 15 | 0 | 0 | | 30 | 30 | 0 | 0 | | 20 | WEAK | WEAK |
| 32 | PEN | 15 | 15 | 0 | 0 | | 30 | 20 | 0 | 10 | | 20/50/80 | ABSENT | ABSENT |
| 33 | PEN | 15 | 15 | 0 | 0 | | 30 | 30 | 0 | 0 | | 20 | WEAK | NORM |
| 34 | PEN | 15 | 10 | 0 | 5 | | 30 | 20 | 5 | 5 | | 20 | WEAK | NORM |
| 35 | NO ASP | 15 | 10 | 0 | 5 | | 30 | 24 | 0 | 6 | | 20 | ABSENT | NORM |
| 36 | NO ASP | 15 | 14 | 0 | 1 | | 30 | 29 | 0 | 1 | | 20 | NORM | NORM |
| 37 | NO ASP | 14 | 13 | 0 | 1 | | 30 | 30 | 0 | 0 | | 20 | NORM | NORM |
| 38 | NO ASP | 15 | 15 | 0 | 0 | | 30 | 30 | 0 | 0 | | 50 | WEAK | WEAK |
| 39 | NO ASP | 15 | 14 | 1 | 0 | | 29 | 29 | 0 | 0 | | 20 | NORM | NORM |
| 40 | PEN | 15 | 15 | 0 | 0 | | 30 | 20 | 10 | 0 | | 20 | NORM | NORM |

*FIG. 3*

| ID# | VOLUNTARY COUGH | NO ASPIRATION INHALATION TEST COUGH | WATER TEST |
|---|---|---|---|
| 2 | + | − | − |
| 3 | − | − | + |
| 4 | + | + | − |
| 7 | + | − | + |
| 10 | − | − | + |
| 12 | − | − | − |
| 13 | − | − | + |
| 15 | + | + | + |
| 18 | + | − | + |
| 20 | − | − | + |
| 22 | + | + | + |
| 25 | − | − | + |
| 26 | − | − | − |
| 27 | − | − | − |
| 29 | − | − | − |
| 30 | + | + | + |
| 31 | + | + | − |
| 35 | + | − | + |
| 36 | − | − | + |
| 37 | − | − | + |
| 38 | + | + | − |
| 39 | − | − | + |

*FIG. 5*

| ID# | VOLUNTARY COUGH | PENETRATION INHALATION TEST COUGH | WATER TEST |
|---|---|---|---|
| 5 | − | − | + |
| 11 | − | − | + |
| 14 | − | − | − |
| 16 | + | + | + |
| 17 | + | − | + |
| 19 | + | − | + |
| 23 | + | − | − |
| 28 | + | − | + |
| 32 | + | + | + |
| 33 | + | − | − |
| 34 | + | − | + |
| 40 | − | − | + |

*FIG. 6*

|  | NORMAL | ABNORMAL | TOTAL |
|---|---|---|---|
| NO ASPIRATION PENETRATION | 16 | 18 | 34 |
| ASPIRATION | 0 | 6 | 6 |
| TOTAL | 16 | 24 | 40 |

$x^2 = 4.706$, $p = 0.035$ BY FISHER EXACT TEST

FIG. 7

|  | PNEUMONIA | NO PNEUMONIA | TOTAL |
|---|---|---|---|
| NORMAL | 0 | 29 | 29 |
| ABNORMAL | 3 | 8 | 11 |
| TOTAL | 3 | 37 | 40 |

$x^2 = 8.55$, $p = 0.017$ BY FISHER EXACT TEST

FIG. 8

|  | ASPIRATION | NO ASPIRATION | TOTAL |
|---|---|---|---|
| UNABLE TO PERFORM | 4 | 3 | 7 |
| ABLE TO PERFORM | 6 | 34 | 40 |
| TOTAL | 10 | 37 | 47 |

$x^2 = 6.317$, $p = 0.029$ BY FISHER EXACT TEST

| FACTOR | LOGISTIC COEFFICIENT | STANDARD ERROR (SE) | COEFF/SE | P |
|---|---|---|---|---|
| VOLUNTARY | -3.88 | 1.91 | -2.04 | 0.05 |
| CONSTANT | 4.98 | 1.85 | 2.69 | |

| VOLUNTARY COUGH | WATER TEST | PREDICTED PROBABILITY OF NO ASPIRATION |
|---|---|---|
| + | - | 0.99 |
| - | + | 0.99 |
| - | - | 1.00 |
| + | + | 0.67 |

FIG. 11

| | MBS + ASP | MBS - ASP |
|---|---|---|
| VOL COUGH + | 6 | 18 |
| VOL COUGH - | 0 | 16 |

- SENS 6/6 = 100%
- SPEC 16/34 = 47.06%
- PVNT 0/16 = 0%
- PVPT 6/24 = 25%

|  | GOLD STAND + | GOLD STAND − |
|---|---|---|
| POSITIVE TEST | a=TRUE | b=FALSE |
| NEGATIVE TEST | c=FALSE | d=TRUE |

- SENS − a/a+c
- SPEC − d/b+d
- PVNT − c/c+d
- PVPT − a/a+b

*FIG. 12*

|  | MBS + ASP | MBS − ASP |
|---|---|---|
| VOL COUGH / H₂O + | 6 | 12 |
| EITHER OR BOTH nl | 0 | 22 |

- SENS 6/6 = 100%
- SPEC 22/34 = 64.70%
- PVNT 0/22 = 0%
- PVPT 6/18 = 33.33%

*FIG. 13*

ASPIRATION SCREENING PROCESS FOR ASSESSING NEED FOR MODIFIED BARIUM SWALLOW STUDY

CROSS REFERENCE TO RELATED APPLICATION

The present application is a continuation application of application Ser. No. 08/559,562, filed Nov. 16, 1995, now U.S. Pat. No. 5,678,563, issued Oct. 21, 1997.

FIELD OF THE INVENTION

The present invention relates in general to the field of speech pathology, and is particularly directed to a process for determining whether a patient is at risk for oral or pharyngeal dysphagia, by means of a cough-based screening process for clinically evaluating the patient's swallow.

BACKGROUND OF THE INVENTION

In order to clinically detect those patients who are at risk for aspiration, speech pathologists currently employ a standard procedure for evaluating a patient's swallow. A normal human swallow can be separated into four phases: 1)—oral preparation, 2)—the oral phase, 3)—the pharyngeal phase, and 4)—the esophageal phase. Patients who have suffered a stroke, traumatic brain injury or neuromuscular disorder (such as MS or ALS) have an increased risk of aspiration, and may have difficulty with either the oral phase, the pharyngeal phase or both, secondary to neurologic deficits. Poor tongue movement in chewing or in the swallow can cause food to fall into the pharynx and into the open airway before the completion of the oral phase. A delay in triggering the pharyngeal swallowing reflex can result in food falling into the airway during the delay when the airway is open. Reduced peristalsis in the pharynx, whether unilateral or bilateral, will cause residue in the pharynx after the swallow that can fall or be inhaled into the airway. Laryngeal or cricopharyngeal dysfunction can lead to aspiration because of decreased airway protection during the swallow.

An abnormal human swallow is termed dysphagia. The oropharyngeal physiology involved in a normal swallow is very complicated, and many different neurological disturbances can disrupt normal swallowing and can cause aspiration of food material, liquid or solid, into the lungs, leading to increased morbidity in hospitalized patients and possible pneumonia. See, for example, the article by Jeri Logemann, entitled: "Swallowing Physiology and Pathophysiology," Otolaryngologic Clinics of North America, Vol. 21, No. 4, November 1988, and the article by L. Kaha et. al., entitled: "Medical Complications During Stroke Rehabilitation," Stroke Vol. 26, No. 6, June 1995.

Speech pathologists have tried many procedures to detect or predict aspiration in patients with neurological deficits. Although the standard bedside swallow exam to screen patients is beneficial for evaluating patients at risk for oral or pharyngeal dysphagia, studies have shown that, when compared to a modified barium swallow (MBS) videofluoroscopic examination, it is neither very specific nor sensitive in detecting aspiration. See, for example, the article by Mark Splaingard et. al. entitled: "Aspiration in Rehabilitation Patients: ideofluoroscopy vs. Bedside Clinical Assessment; Archives of Physical Medicine and Rehabilitation, Vol. 69, August, 1988, and the article by P. Linden, et. al., entitled" "The Probability of Correctly Predicting Subglottic Penetration from Clinical Observations", Dysphagia, 8: pp 170–179, 1993.

As discussed in the above-referenced Logemann article, and also in an article entitled: "Aspiration of High-Density Barium Contrast Medium Causing Acute Pulmonary Inflammation—Report of Two Fatal Cases in Elderly Women with Disordered Swallowing," by C., Gray et al, Clinical Radiology, Vol. 40, 397–400, 1989, videofluoroscopic evaluations are more costly than bedside evaluations and videofluoroscopy is not entirely without risk. Because of the poor predictability of the present bedside exams, the MBS is being used more and more with its increased reliability for diagnosing aspiration. Many studies using videofluoroscopy have tried to pinpoint the exact anatomical or neurological deficit causing the dysphagia, as well as what stage of the swallow is primarily affected in different disorders.

Patients that have a head injury, stroke or other neuromuscular disorder can aspirate before, during, or after the swallow, and a high percentage can be silent aspirators. Unfortunately, these patients might not display any indication of aspiration during a clinical exam but can be detected by the MBS, as discussed in the Logemann article and in an article by C. Lazurus et al, entitled: "Swallowing Disorder in Closed Head Trauma Patients," Archives of Physical Medicine and Rehabilitation, Vol. 68, February, 1987, an article by J. Logemann, entitled: "Effects of Aging on the Swallowing Mechanism," Otolaryngologic Clinics of North America, Vol. 23, No. 6, December 1990, and an article by M. DeVito et. al., entitled: "Swallowing Disorders in Patients with Prolonged Orotracheal Intubation or Tracheostomy Tubes," Critical Care Medicine, Vol. 18, No. 12, 1990.

The bedside swallow exam performed by most speech pathologists evaluates history, respiratory status, level of responsiveness and an oral exam. The oral examination includes a detailed evaluation of the muscles of mastication, lips, tongue, palate, position patient tested in as well as the swallowing evaluation. Sensation, various movements and strength are carefully evaluated. In the pharyngeal stage, the patient is tested for a dry swallow, thin liquid, thick liquid, pureed textures and solid textures.

A typical bedside exam looks for nasal regurgitation, discomfort or obstruction in the throat or multiple swallows, as well as any visible signs that may indicate risk for aspiration, gurgling, impaired vocal quality, and coughing. The bedside exam results are then analyzed to determine whether the patient should have an MBS study to evaluate swallowing physiology and to rule out aspiration. Although the bedside exam is very thorough, and can identify patients who are at risk for or have dysphagia, it is not effective in determining which patients will aspirate.

In addition to the foregoing, speech pathologists have historically had difficulty studying the sensory afferents of the larynx involved in airway protection. As described in an article by J. Widdicombe et al, entitled: "Upper Airway Reflex Control," Annual New York Academy of Science, Vol. 533, 252–261, 1988, the sensory afferents for general coughing travel the internal branch of the superior laryngeal nerve. A patient may have a voluntary cough present with the efferent motor system intact, but not have any sensation on the larynx secondary to the afferents becoming completely or partially affected, which would be indicative of risk for silent aspiration.

As described above, the MBS test is of value to patients that silently aspirate. The difficulty arises in deciding which patients should have an MBS test. Not all patients with a closed head injury or a stroke will aspirate. Further, it is not economically realistic to evaluate all patients with neurologic deficits for aspiration using an MBS test. It would be beneficial therefore to have a method to clinically screen patients with neurologic deficits that have dysphagia, and to more accurately predict which patients are at risk of aspiration and which patients are not.

SUMMARY OF THE INVENTION

In accordance with the present invention, the shortcomings of the above-described conventional processes employed by speech pathologists to detect aspiration in patients with neurological deficits are effectively remedied by a cough-based screening process which is operative to clinically detect a (stroke) patient who is at risk for aspiration in both oral and pharyngeal phases of the human swallow. The inventive screening methodology is able to identify those patients who require an MBS test in order to rule out aspiration, and which patients do not need an MBS.

The initial step according to the cough-based screening process of present invention involves a pharyngeal test, in which the patient is given two separate tasks to perform. The patient will have been diagnosed as having had a stroke, and is potentially scheduled to undergo a modified barium swallow (MBS) test. The patient should not be one with a history of asthma or on supplemental oxygen for dyspnea. A speech pathologist performs a preliminary general bedside swallow evaluation and also tests for cognition, voice quality and cranial nerves.

In the first step of the pharyngeal test the patient is required to voluntarily cough. The patient's ability to voluntarily cough is a reflection of the function of the patient's efferent motor system, and is graded by the testing pathological specialist as either normal or decreased, if the patient is able to successfully cough. The patient may then optionally be administered a water-holding test, in which the patient is asked to hold a given amount of water in the patient's mouth for a given period of time.

If the patient is not able to cough voluntarily, the patient is subjected to an inhalation cough test, in which a sensory innervation to the patient's larynx is tested. As will be described, this sensory innervation test of the patient's larynx is carried out by stimulating nociceptor (irritant) and C-fibre receptors, using an aerosol chemostimulant that is inhaled through the patient's mouth.

In accordance with a preferred embodiment of the present invention, the aerosol inhalant, which may be delivered by a standard aerosol inhaler, comprises an atomized solution of tartrate mixed with saline. Although other receptor specific chemostimulants may be employed, studies involving inhaling tartate, reveal that tartrate will stimulate a cough 100% of the time in normal individuals. Further, tartate is considered safe, does not cause pain or discomfort, and has not been shown to cause bronchoconstriction or complications in asthmatics when inhaled in an aerosol form.

During the inhalation cough test, the aerosol stimulant is injected into the patient's mouth by a respiratory therapist, using a nebulizer for a relatively brief period of time. The patient is tested a maximum of three times at different stimulant strengths until a cough is elicited. During each successive stimulant application, the patient receives progressively increasing concentrations of the aerosol for the prescribed period of time by tidal breathing at one minute intervals using successively increasing percentage concentrations.

In response to the patient coughing as a result of the inhaled aerosol stimulant, the inhalation cough test is terminated, regardless of the percentage of concentrations used. The patient's response to the inhalation test is graded as either a low pneumonia risk (if the patient coughs immediately in response to the initial aerosol spray and the cough appears strong or normal) or a high pneoumonia risk (where the cough appears weak or the patient does not readily cough in response to the initial concentration spray, but requires a more concentrated aerosol application).

Upon completion of the inhalation cough test, the water holding test is conducted. During the water-holding test, the patient is required to take two separate volumes of water into the mouth and hold the water for a specified period of time. Two separate volumes of water are used, since aspiration can occur with large volumes or smaller volumes separately. During the water holding test, the patient is instructed not to swallow any of the water and, at the end of the specified time, to return the held water to a measuring receptacle. Any water that is lost out of the patient's mouth as a result of a facial droop or poor labial control is collected and measured. Also, the total water returned to the measuring receptacle is calculated, in order to determine if water may have spilled over into the pharynx should there be any of the original volume of water not recollected.

BRIEF DESCRIPTION OF THE DRAWINGS

FIG. 2 diagrammatically illustrates the use of an aerosol inhaler in the inhalation cough phase of the process of the present invention;

FIGS. 3–6 diagrammatically tabulate the results of conducting the screening process of the present invention for individual ones of a group of stroke patients;

FIG. 7 tabulates the results of the voluntary cough test of the present invention for forty stroke patients into normal and abnormal coughs, classified as no aspiration and penetration combined together versus an aspiration group;

FIG. 8 tabulates the results of the inhalation cough test of the present invention for forty stroke patients showing those diagnosed as developing pneumonia and no pneumonia, classified as normal and abnormal groups;

FIG. 9 tabulates the classification of MBS for two groups of stroke patients including forty patients who were able to perform and an additional seven patients who were not able to perform the tests, in terms of aspiration and no aspiration;

FIG. 10 tabulates multivariate association by stepwise logistic regression for no aspiration diagnosis;

FIG. 11 provides a matrix relationship between MBS aspiration (+) and (−) and a voluntary cough (+) and (−);

FIG. 12 tabulates Gold Standard ratio definitions; and

FIG. 13 provides a matrix relationship between MBS aspiration (+) and (−) and a voluntary cough/water test combinted (+) and either or both nl.

DETAILED DESCRIPTION

As described briefly above, the steps of the cough-based screening process of the present invention are operative to clinically detect a (stroke) patient, who is at risk for aspiration (one of the characteristics of dysphagia), by evaluating the patient for both oral and pharyngeal phases of the human swallow. The inventive screening methodology is able to identify those patients who require an MBS test in order to rule out aspiration, and which patients do not need an MBS for that purpose. In addition, the invention quantifies the risk of aspiration based on the results of the bedside screen test compared to the MBS test.

Figure 1:
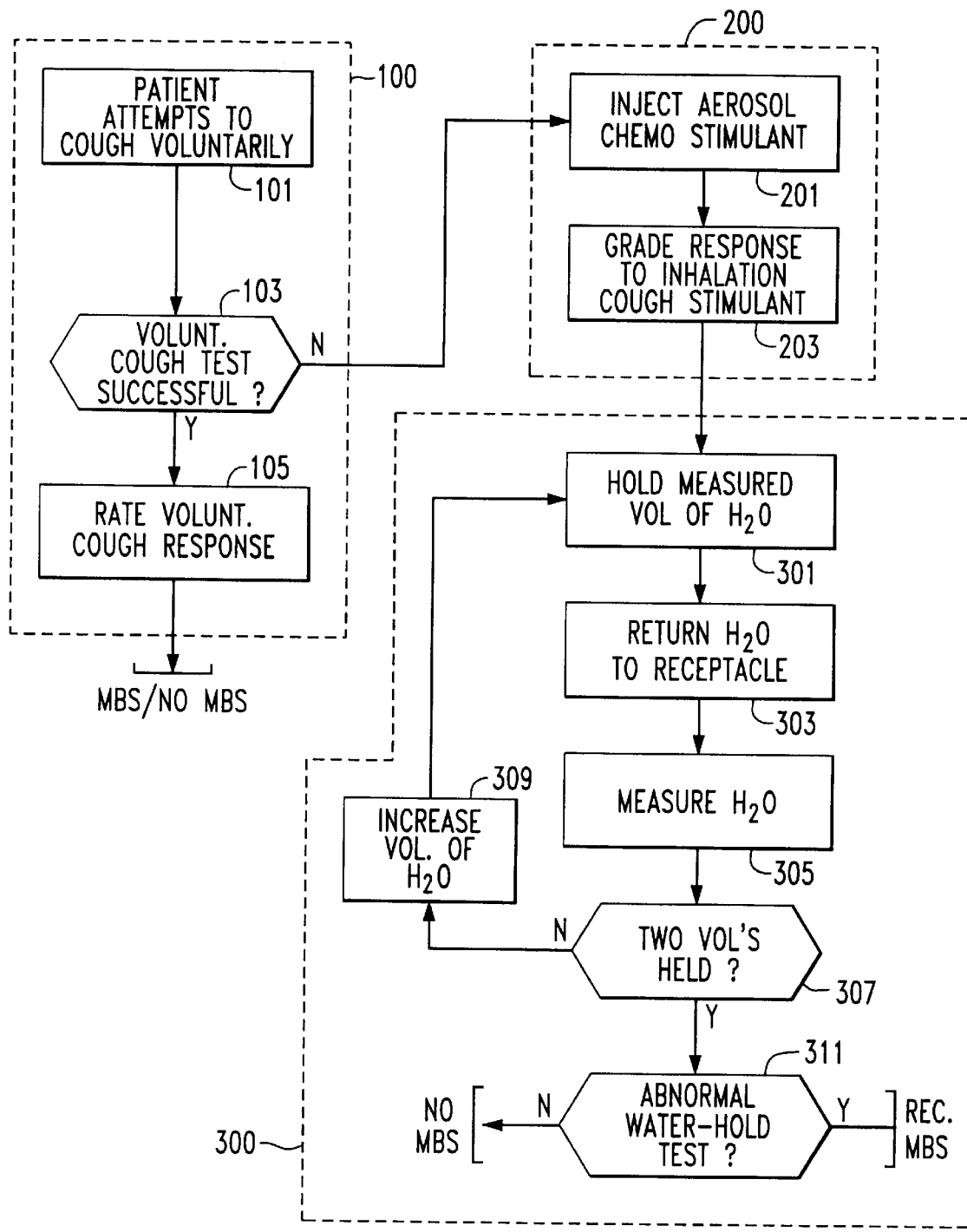
FIG. 1 is a flow diagram of the cough-based screening process for determining whether a patient is at risk for oral or pharyngeal dysphagia in accordance with the present invention.

Referring now to the flow diagram of FIG. 1, the cough-based screening process according to the present invention begins with a pharyngeal test, shown at 100, in which the patient is given two separate physiologic tasks to perform. Typically, the patient will be an adult individual, who has been diagnosed as having had a stroke, has already been scheduled to undergo a (not yet administered) modified barium swallow (MBS) test, and is able to follow commands and give informed consent to participate. The patient should not be one with a history of asthma or on supplemental oxygen for dyspnea. A speech pathologist performs a preliminary general bedside swallow evaluation and also tests for cognition, voice quality and cranial nerves.

The first step in the pharyngeal test 100 (STEP 101) is to ask the patient to voluntarily cough. The patient's ability to voluntarily cough is a reflection of the function of the patient's efferent motor system, and is characterized or scored by the testing pathological specialist as either normal, decreased or absent. If the patient is able to successfully cough (the answer to query STEP 103 is YES), the patient's response is rated in step 105 as either normal or decreased, depending upon the testing pathologist's estimation of the cough response. The patient may then optionally be administered a water-holding test, shown at 300 and to be described, in which the patient is asked to hold a given amount of water in the patient's mouth for a given period of time.

If the patient does not pass the voluntary cought test, namely, is not able to cough voluntarily or the cough is decreased (the answer to query STEP 103 is NO), the voluntary cough is rated as absent or decreased, and the patient is then subjected to an inhalation cough test 200, in which a sensory innervation to the patient's larynx is tested. As noted briefly above, this sensory innervation test of the patient's larynx is carried out by stimulating nociceptor (irritant) and C-fibre receptors, using an aerosol chemostimulant that is inhaled through the patient's mouth. As diagrammatically illustrated in FIG. 2, during the inhalation cough test, the patient wears a noseclip 20.

There is increasing evidence that reflexes for cough and bronchoconstriction are mediated by different pathways, and there are numerous chemostimulants which are receptor specific. See, for example, the article entitled "Regional Sensitivity of the Respiratory Tract to Stimuli Causing Cough and Reflex Bronchoconstriction," by J. Karlson et. al, Respiratory Medicine, 85 (Supplement A): 47–50, 1991, the text "Cough Receptor Sensitivity and Bronchial Responsiveness in Normal and Asthmatic Subjects," European Respiratory Journal, 56: 291–295, 1992, and the article entitled: "Effects of Methacholine Induced Bronchoconstriction and Procateral-Induced Bronchodilation on Cough Receptor Sensitivity to Inhaled Capsaicin and Tartaric Acid," by M. Fujimura al., Thorax, 47: pp 441–445, 1992.

Figures 2, 4:
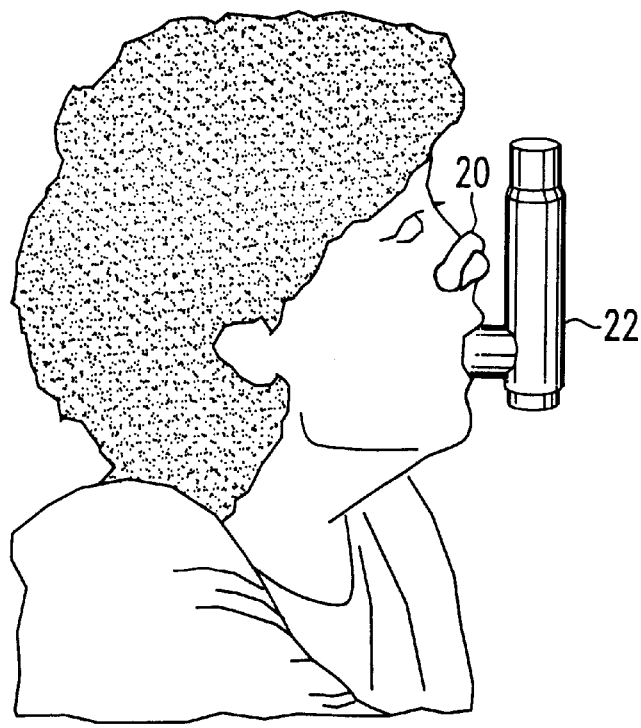

In accordance with a preferred embodiment of the present invention, the aerosol inhalant, which may be delivered by a standard aerosol inhaler, such as a commerically available Bennett Twin nebulizer, shown at 22 in FIG. 2, comprises an atomized solution of tartrate mixed with saline. Although other receptor specific chemostimulants may be employed, studies involving inhaling tartate, as described in the article entitled: "Cough Receptor Sensitivity and Bronchial Responsiveness in Normal and Asthmatic Subjects," by M. Fujimura et al, European Respiratory Journal, 56: 291–295, 1992, in the text entitled: "Clinical Toxicology of Commercial Products, Tartaric Acid," Fifth Ed., p563, Williams and Wilkins, Baltimore/London, in the reference text entitled: "Martindale: The Extra Pharmacopoedia," Twenty Ninth Edition, The Pharmaceutical Press, London, 1989, and in the above-referenced Linden article have revealed that tartrate will stimulate a cough 100% of the time in normal individuals.

Moreover, tartate is considered safe, does not cause pain or discomfort, and has not been shown to cause bronchoconstriction or complications in asthmatics when inhaled in an aerosol form. See, for example, the article by M. Fujimura et al, entitled: "Sex Difference in the Inhaled Tartaric Acid Cough Threshold in Non-Atopic Healthy Subjects," Thorax, 45: 633–634, and the previously referenced articles by M. Fujimura et al, and the Williams and Wilkins, and Martindale texts.

During the first step (STEP 201) of the inhalation cough test 200, the aerosol chemostimulant is injected into the patient's mouth by a respiratory therapist, using nebulizer 22 for a prescribed period of time (e.g., on the order of 15 seconds). The nebulizer output spray rate may be on the order of 0.2 ml/min. as a non-limiting example. During STEP 201, the patient is tested a maximum of three times at different stimulant strengths until a cough is elicited. During each successive chemostimulant application, the patient receives progressively increasing concentrations of the aerosol for the prescribed period of time by tidal breathing at one minute intervals using successively increasing percentage concentrations (e.g. 20, 50 and 80 percent).

Once the patient elicits a cough as a result of the inhaled aerosol stimulant in STEP 201, the inhalation cough test is terminated, regardless of the percentage of concentrations used. Next, the patient's response to the inhalation test is graded in STEP 203 as either a low pneumonia risk (as in the case where the patient coughs immediately in response to the initial aerosol spray) or a high pneumonia risk (in the case where a cough is present but decreased, or the patient does not readily cough in response to the initial concentration spray, but requires a more concentrated aerosol application).

Upon completion of the inhalation cough test 200, the water holding test 300 is conducted. As noted earlier, the water-holding test may also be carried out after or in parallel with the voluntary cough test 100, described above. In the water-holding test, the patient is required to take two separate volumes of water into the mouth and hold the water for a specified period of time (e.g. on the order of ten seconds). Two separate volumes of water are used, since aspiration can occur with large volumes or smaller volumes separately, as described in the previously referenced Logemann article.

During STEP 301 of the water holding test 300, the patient is instructed not to swallow any of the water and, at the end of the specified time (STEP 303) to return it to a measuring receptacle. The first volume of water given to the patient may be on the order of 15 ml, as a non-limiting example. Any water that is lost out of the patient's mouth as a result of a facial droop or poor labial control is collected and measured (STEP 305). In addition, the total water returned to the measuring receptacle is calculated, in order to assess what water may have spilled over into the pharynx if any of the volume is missing. In query STEP 307, a determination is made whether the water holding test has been conducted for two separate volumes of water. If the answer to query STEP 307 is NO, a second vial of water is given to the patient in step 309, and the process returns to step 301. The second volume of water may be on the order of 30 ml, as a non-limiting example. If the answer to query STEP 307 is YES, the process proceeds to query STEP 311.

In query STEP 311, based upon the results of STEP 305, a determination is made as to whether the patient has passed the water-holding test, namely—no water has been lost out of the patient's mouth and no water has spilled over into the patient's pharynx. If the answer to query STEP 311 is NO, it is concluded that the patient need not be given an MBS test. (In a test evaluation of performing the water test-holding test steps on twenty normal individuals, ages 30–72, for both volumes, no changes in volume return (p<0.01) were measured in STEP 305.) If, however, the answer to query STEP 311 is YES (there has been spillage or leakage from the patient's mouth), then it is concluded that the patient should be given an MBS test.

EXAMPLE

FIGS. 3–12 diagrammatically tabulate the results of conducting the foregoing described methodology, using the component concentrations and volumes of tartrate saline and water described above for a group of stroke patients of the various ages listed. In the Figures, each (+) indicates that the patient failed the specified phase (voluntary cough, inhalation cough, water-holding test) of the process, while a (−) indicates that the patient passed that phase of the process.

In addition to the individual patient responses listed in FIGS. 3–6, FIG. 7 tabulates the results of the voluntary cough test for the forty stroke patients into normal and abnormal coughs, classified as no aspiration and penetration combined together versus the aspiration group.

FIG. 8 tabulates the results of the inhalation cough test for the forty patients showing those diagnosed as developing pneumonia and no pneumonia, classified as normal and abnormal groups. It may be noted that no patient who exhibited a normal cough response to this test developed pneumonia.

FIG. 9 tabulates the classification of MBS for two groups of patients including the forty patients who were able to perform and an additional seven patients who were not able to perform the tests (for a total of forty-seven patients), in terms of aspiration and no aspiration.

FIG. 10 tabulates multivariate association by stepwise logistic regression for no aspiration diagnosis. FIG. 10 reveals no predicted probablity of aspiration for any patient who passed the voluntary cough and water-holding tests.

FIG. 11 provides a matrix relationship between MBS aspiration (+) and (−) and a voluntary cough (+) and (−). Associated with the matrix of FIG. 11 are the ratios of sensitivity (SENS), specificity (SPEC), predictive value of negative test (PVNT) and predictive value of positive test (PVPT), defined in accordance with the Gold Standard ratio definitions listed in FIG. 12.

FIG. 13 provides a matrix relationship between MBS aspiration (+) and (−) and a voluntary cough/water test combinted (+) and either or both nl. Also associated with the matrix of FIG. 13 are the ratios of sensitivity (SENS), specificity (SPEC), predictive value of negative test (PVNT) and predictive value of positive test (PVPT).

As will be appreciated from the foregoing description, whether a (stroke) patient is at risk for oral or pharyngeal dysphagia is readily determined in accordance with the cough-based screening process of the present invention, which is able to identify those patients who require a modified barium swallow test in order to rule out aspiration, and which patients do not need a modified barium swallow test. By requiring a patient who is unable to cough voluntarily to inhale an aerosol that stimulates a sensory innervation of the patient's larynx, and thereby causes the patient to cough involuntarily, the patient can be graded to determine whether the patient is at risk to pneumonia. Supplementing the cough tests with the water-holding test allows a determination of whether the patient is permitted to be given a modified barium swallow test.

While we have shown and described an embodiment in accordance with the present invention, it is to be understood that the same is not limited thereto but is susceptible to numerous changes and modifications as known to a person skilled in the art, and we therefore do not wish to be limited to the details shown and described herein but intend to cover all such changes and modifications as are obvious to one of ordinary skill in the art.

What is claimed:

1. A method of evaluating a patient comprising the steps of:

(a) supplying to the throat of the patient a medium that stimulates a sensory innervation of the patient's throat, thereby causing the patient to cough involuntarily;

(b) evaluating the involuntary cough of the patient in step (a) to determine a prescribed physiological condition of said patient; and (c) monitoring the ability of the patient to hold water in the patient's mouth for a prescribed period of time, and identifying said patient as one who should be given a modified barium swallow test in accordance with whether said patient is able to hold water in the patient's mouth for said prescribed period of time.

2. A method according to claim 1, wherein said medium supplied to the patient's throat in step (a) contains a chemical that is effective to stimulate nociceptor (irritant) and C-fibre receptors in the patient's throat.

3. A method according to claim 1, wherein said medium in step (a) contains tartrate mixed with saline.

4. A method according to claim 1, wherein said medium supplied in step (a) contains respectively different stimulant strengths of a chemical that is effective to stimulate a sensory innervation of the patient's larynx.

5. A method according to claim 1, wherein step (a) comprises supplying to the patient's throat an aerosol containing progressively increasing concentrations of a chemostimulant that is effective to stimulate a sensory innervation of the patient's larynx.

6. A method according to claim 5, wherein, during step (a) said patient receives said progressively increasing concentrations of said aerosol by tidal breathing at prescribed time intervals.

7. A method, of evaluating a patient comprising the steps of:

(a) supplying to the throat of the patient a medium that stimulates a sensory innervation of the patient's throat, thereby causing the patient to cough involuntarily; and (b) evaluating the involuntary couch of the patient in step (a) to determine a prescribed physiological condition of said patient, and wherein step (a) comprises supplying to the patient's throat an aerosol containing progressively increasing concentrations of a chemostimulant that is effective to stimulate a sensory innervation of the patient's larynx, and wherein step (b) comprises grading the cough of the patient as either a low pneumonia risk if the patient's cough appears normal in response to the initial aerosol spray, or a high pneumonia risk where the patient has a decreased or weak cough in response to the initial concentration spray or requires a more concentrated aerosol application to elicit a cough.

8. A method, of evaluating a patient comprising the steps of:

(a) supplying to the throat of the patient a medium that stimulates a sensory innervation of the patient's throat, thereby causing the patient to cough involuntarily; and (b) evaluating the involuntary cough of the patient in step (a) to determine a prescribed physiological condition of said patient, and wherein step (b) comprises evaluating the involuntary cough of the patient in step (a) to determine whether said patient is at risk for pneumonia.

* * * * *